US00PP10312P

United States Patent [19]

Turc

[11] Patent Number: Plant 10,312

[45] Date of Patent: Mar. 31, 1998

[54] ALSTROMERIA PLANT NAMED 'LOIRICHA'

[75] Inventor: Jean Pierre Turc, Mazé, France

[73] Assignee: Selection New Plant Sarl, Le Luc, France

[21] Appl. No.: 788,266

[22] Filed: Jan. 24, 1997

[51] Int. Cl.[6] ..... A01H 5/00

[52] U.S. Cl. ..... Plt./87.1

[58] Field of Search ..... Plt./87.1

[56] References Cited

U.S. PATENT DOCUMENTS

P.P. 6,197 6/1988 Van Andel ..... Plt./87.1

P.P. 9,446 1/1996 Van Andel ..... Plt./87.1

P.P. 9,448 2/1996 Van Andel ..... Plt./87.1

*Primary Examiner*—James R. Feyrer

*Assistant Examiner*—Kent L. Bell

*Attorney, Agent, or Firm*—Burns, Doane, Swecker & Mathis, L.L.P.

[57] ABSTRACT

A new and distinct variety of Alstroemeria plant is provided which abundantly forms attractive double large bright red flowers. The flowers are borne on long peduncles as an umbel. The plant propagates well by the division of roots. The plant can be grown as distinctive ornamentation under mild temperature conditions.

1 Drawing Sheet

SUMMARY OF THE INVENTION

The new variety of Alstroemeria was created by artificial pollination wherein two parents were crossed which previously had been studied in the hope that they would contribute the desired characteristics. The female parent (i.e., the seed parent) of the new variety was the 'Turcalva' variety (non-patented in the United States). The 'Turcalva' variety is marketed in Europe under the VALERIE trademark. The male parent (i.e., the pollen parent) of the new variety was the 'Aurantiaca Orange' variety (non-patented in the United States). The parentage of the new variety can be summarized as follows:

'Turcalva'×'Aurantiaca Orange'.

The seeds resulting from the above pollination were sown and small plants were obtained which were physically and biologically different from each other. Selective study resulted in the identification of a single plant of the new variety.

It was found that the new Alstroemeria plant of the present invention possesses the following combination of characteristics:

(a) forms in abundance attractive large bright red flowers on long peduncles as an umbel,
(b) propagates well by the division of roots, and
(c) is particularly suited for growing as a distinctive ornamental plant under mild temperature conditions.

The new variety has been found to undergo asexual propagation in France by the separation or splitting of roots. Asexual propagation by the above-mentioned methods as performed in France has shown that the characteristics of the new variety are strictly transmissible from one generation to another.

The new variety has been named the 'Loiricha' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The Alstroemeria plants of the new variety were sixteen months of age and were observed during February while growing indoors at Mazé, Maine et Loire, France.

FIG. 1—illustrates a specimen of two floral buds;

FIG. 2—illustrates a specimen of a floral bud in the course of opening;

FIG. 3—illustrates a specimen of a flower in the course of opening;

FIG. 4—illustrates a specimen of an open flower;

FIG. 5—illustrates specimens of external floral petals—plan view—obverse;

FIG. 6—illustrates a specimen of external floral petals—plan view—reverse;

FIG. 7—illustrates specimens of central floral petals—plan view—obverse;

FIG. 8—illustrates specimens of central floral petals—plan view—reverse;

FIG. 9—illustrates specimens of stamens;

FIG. 10—illustrates a specimen of an upper leaf—plan view—obverse;

FIG. 11—illustrates a specimen of an upper leaf—plan view—reverse;

FIG. 12—illustrates a specimen of a lower leaf—plan view—obverse;

FIG. 13—illustrates a specimen of a lower leaf—plan view—reverse; and

FIG. 14—illustrates a specimen of a stem.

DETAILED DESCRIPTION

Figures 1, 2, 3, 4, 5, 6, 7, 8, 9, 10, 11, 12, 13, 14:
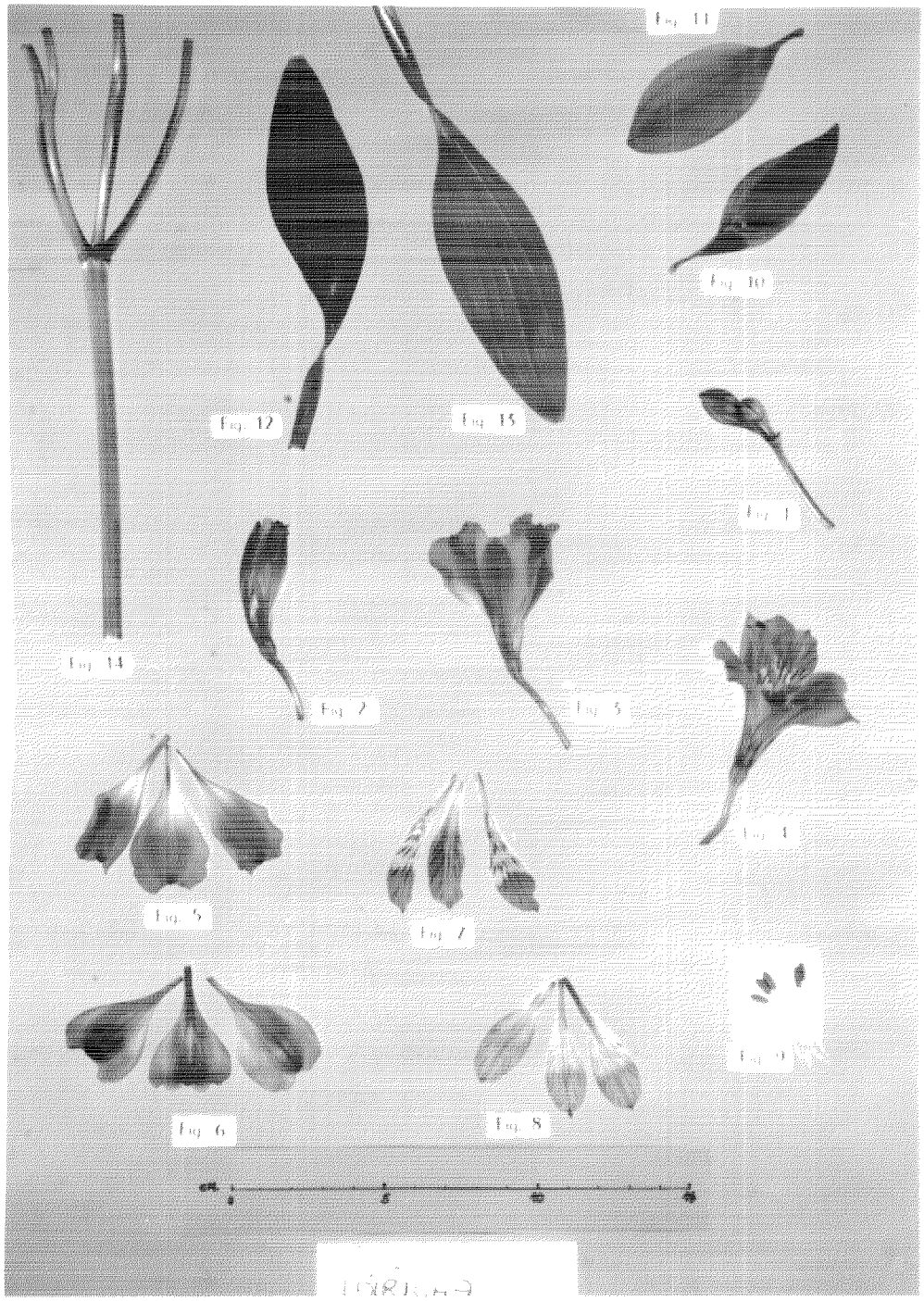

The chart used in the identification of the colors is that of The Royal Horticultural Society (R.H.S. Colour Chart). The terminology which precedes reference to the chart has been added in some instances to indicate the corresponding colors in more common terms. The description is based on the observation of sixteen month-old specimens of the new variety during February while growing indoors at Mazé, Maine et Loire, France.

Origin: Artificial pollination.

Parentage:

*Female.*—'Turcalva' which is marketed under the VALERIE trademark in Europe.

*Male.*—'Aurantiaca Orange'.

Classification: Alstreomeria hybrid.

Plant:

*Form.*—Shrub.

*Height.*—Size: approximately 1.5 to 2 m. on average.

*Habit.*—Fast growing with vigorous upright stems of good strength.

Foliage:

*Number of leaves.*—Approximately 18 to 23 on average.

*Leaf shape.*—Elliptical.

*Leaf size.*—Approximately 11 to 11.5 cm. in length and approximately 2.5 to 3 cm. in width.

*Texture.*—Smooth and glossy.

*Color.*—Adult foliage is medium green, Green Group 137A to Green Group 137B on the upper surface, and light green, Greyed-Green Group 191A on the under surface.

*Rhizome color.*—Milky white, near White Group 155D.

*Rhizome size.*—Variable with growing season.

Inflorescence:

*Peduncle length.*—Commonly approximately 13 to 14 cm.

*Peduncle disposition.*—Erect and upright.

*Peduncle color.*—Yellow-Green Group 144B.

*Buds.*—Shape: oblong and pear-shaped. Size: approximately 2.5 to 3 cm. in length, and approximately 1 cm. in diameter.

*Blooming habit.*—Continuous with no substantial interruption.

*Blooms.*—Size: large in an umbel. Diameter: approximately 6 cm. Depth: approximately 6 cm. Borne: singly on a stem. Form: cup-shaped. Number of petals: six. Arrangement: generally two concentric circles of three petals each. Texture: soft. Color (in course of opening): Central petals (obverse): near Yellow Group 5B towards the center, and terminating in an area that is widely suffused with Red-Purple Group 58A. Discontinuous dark stripes also are present (as illustrated). Central petals (reverse): near Red Group 52C, and commonly with a green area at the middle of the tip (as illustrated). External petals (obverse): Yellow Group 7A, widely suffused with Red Group 51B, and with some whitening towards the base of the petal (as illustrated). External petals (reverse): near Red Group 51B, and commonly with a greenish line (as illustrated) that divides the petal longitudinally. Color (after full bloom): whitening tends to occur. Lasting quality: approximately 4 to 5 weeks on the plant, and approximately 3 weeks when the blossoms are cut and are placed in a vase. Stamens: commonly six in number with one being arranged opposite each petal. Anthers: before dehiscence yellowish-brown and after dehiscence grey-brown in coloration, and commonly approximately 7 mm. in length. Filaments: pinkish in coloration and approximately 4 cm. in length. Pollen: yellowish in coloration. Pistils: commonly one. Styles: pinkish-purple in coloration and approximately 3.5 cm. in length. Stigmas: pinkish in coloration. Fruit: brownish-green in coloration at maturity, rounded, and commonly infertile.

Development

*Propagation.*—Propagates well through the division of roots.

*Resistance to diseases.*—Good.

*Resistance to frost.*—None with the best culture conditions being exhibited above 20° C.

I claim:

1. A new and distinct variety of Alstroemeria plant characterized by the following combination of characteristics:

(a) forms in abundance attractive large bright red flowers on long peduncles as an umbel;

(b) propagates well by the division of roots; and (c) is particularly suited for growing as a distinctive ornamental plant under mild temperature conditions;

substantially as herein shown and described.

* * * * *